United States Patent [19]

Meisinger et al.

[11] 4,178,169
[45] Dec. 11, 1979

[54] DIPHENYL SULFIDE, SULFOXIDE AND SULFONE PLANT GROWTH REGULATORS

[75] Inventors: Robert H. Meisinger, Glen Ellyn, Ill.; Pyung K. Yu, Miami, Fla.

[73] Assignee: Rohm and Haas Company, Philadelphia, Pa.

[21] Appl. No.: 905,314

[22] Filed: May 12, 1978

[51] Int. Cl.² ............................................. A01N 5/00
[52] U.S. Cl. ......................................... 71/98; 71/103; 71/DIG. 1
[58] Field of Search .............................. 71/76, 98, 103

[56] References Cited
U.S. PATENT DOCUMENTS

| 3,954,442 | 5/1976 | Becker et al. | 71/98 X |
| 4,023,958 | 5/1977 | Rohe et al. | 71/103 |

*Primary Examiner*—Catherine L. Mills
*Attorney, Agent, or Firm*—Susan Borden Evans

[57] ABSTRACT

Compounds of the formula

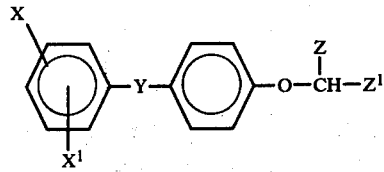

wherein
  X is hydrogen, halogen, trifluoromethyl, or nitro
  $X^1$ is hydrogen, halogen, trifluoromethyl, cyano, carbamoyl, alkyl, alkoxy, alkoxycarbonyl, alkylcarbonyl, alkylsulfonyl, or amino,
  Y is —S—, —SO—, or —SO$_2$—,
  Z is hydrogen or alkyl and
  $Z^1$ is carboxy, or a salt thereof, carbalkoxy, cyano or carbzmoyl,
are useful in regulating the growth of plants when applied to the plant, plant habitat, or plant seeds.

15 Claims, No Drawings

DIPHENYL SULFIDE, SULFOXIDE AND SULFONE PLANT GROWTH REGULATORS

This invention relates to the use of certain diphenyl sulfides, sulfoxides, and sulfones as plant growth regulators.

In the growth cycle of many agronomic and ornamental plant species, certain undesirable or unwanted growth patterns take place. For example, in many ornamental species, compact shape or limited growth is desirable. In some crop species, undesirable secondary growth occurs. In addition, it is often advantageous to induce increased flowering or improved fruiting in other species. Consequently, various chemical compounds have been developed which function as growth regulators in attaining some of these objectives. However, the commercially available chemical growth regulators are deficient in one or more respects, such as is causing undue phytotoxicity, in inducing undesirable side effects, or in lacking either a broad spectrum of utility or utility in specific agronomic species. It has now been found that certain diphenyl sulfides, sulfoxides, and sulfones have valuable activity in regulating the growth and development of plants.

The compounds useful in the present invention have the formula

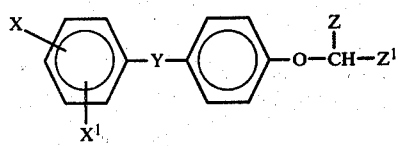 (I)

wherein

X is a hydrogen atom, a halogen atom, preferably a chlorine atom, a trifluoromethyl group, or a nitro group, X' is a hydrogen atom, a halogen atom, preferably a chlorine atom, a trifluoromethyl group, a cyano group, a carbamoyl group, an alkyl group, preferably a methyl group, an alkoxy group, preferably a methoxy group, an alkoxycarbonyl group, preferably a $(C_1-C_4)$ alkoxycarbonyl group, most preferably a methoxycarbonyl or an ethoxycarbonyl group, an alkylcarbonyl group, preferably a methylcarbonyl group, an alkylsulfonyl group, preferably a methanesulfonyl group, or an amino group, Y is a group of the formula —S—, —SO—, or —SO$_2$—, Z is a hydrogen atom or an alkyl group, preferably having 1 to 4 carbon atoms, most preferably a methyl group, and $Z^1$ is a carboxy group (—COOH) or an agronomically-acceptable salt thereof, a cyano group, or a group of the formula —COR, wherein R is an alkoxy group, preferably having 1 to 12 carbon atoms, an aralkoxy group, preferably having 7 to 12 carbon atoms, most preferably a phenyl$(C_1-C_5)$alkoxy group, an alkoxyalkoxy group, preferably having 1 to 6 carbon atoms in each alkoxy moiety, an alkenyloxy group, preferably having 3 to 5 carbon atoms, an amino group, an alkylamino group, preferably having 1 to 4 carbon atoms, or a dialkylamino group, preferably having 1 to 4 carbon atoms in each alkyl substituent.

In a preferred embodiment of the invention X is a halogen atom or a trifluoromethyl group and $X^1$ is a hydrogen atom, a halogen atom, or a cyano group. In another preferred embodiment of the invention, Y is a group of the formula —S— or —SO—, most preferably —SO—, X is a trifluoromethyl group, $X^1$ is a hydrogen atom or a halogen atom, most preferably a chlorine atom, Z is a methyl group, and $Z^1$ is a group of the formula —COR, wherein R is a $(C_1-C_{12})$alkoxy group.

When $Z^1$ is a carboxy group, either the free acid or the salt can be used. Among the agronomically-acceptable salts are the alkali metal salts, such as sodium and potassium salts, alkaline earth metal salts, such as magnesium, calcium and barium salts, heavy metal salts, such as copper and zinc salts, amine salts, such as ammonium, ethanolammonium, diethanolammonium, triethanolammonium, triethylammonium, dimethylammonium, diisopropylammonium, t-butylammonium, t-octylammonium, and similar salts.

Examples of compounds of the invention embraced by Formula I include:

Ethyl 2-[4-(2-chloro-4-trifluoromethylphenylthio)-phenoxy]propionate

Ethyl 2-[4-(2-chloro-4-trifluoromethylphenylsulfinyl)-phenoxy]propionate

2-[4-(2-bromo-4-trifluoromethylphenylthio)phenoxy]-propionic acid, and its salts 2-Methoxyethyl 2-[4-(2-trifluoromethylphenylsulfinyl)-phenoxy]propionate Ethyl 2-[4-(4-chlorophenylthio)phenoxy]propionate Allyl 2-[4-(2-chloro-4-cyanophenylthio)phenoxy]butyrate n-Propyl 2-[4-(2-nitro-4-trifluoromethylphenylsulfonyl)phenoxy]propionate 2-[4-(2-Nitrophenylsulfinyl)phenoxy]propionamide 2-[4-(3,4-Dichlorophenylthio)phenoxy]propionitrile N,N-Dimethyl-2-[4-(3-trifluoromethylphenylsulfonyl)-phenoxy]butyramide Sodium 2-[4-(2-chloro-4-trifluoromethylphenylsulfinyl)phenoxy]propionate Ethyl 2-[4-(2-trifluoromethylphenylthio)phenoxy]propionate Ethyl 2-[4-(2-carbamoyl-4-trifluoromethylphenylthio)-phenoxy]propionate Ethyl 2-[4-(2-chloro-4-trifluoromethylphenylsulfonyl)-phenoxy]propionate Methyl 2-[4-(2-chloro-4-trifluoromethylphenylsulfonyl)2-methylphenoxy]crotonamide Ethyl 2-[4-(3-trifluoromethylphenylthio)phenoxy]propionate N,N-Dimethylaminoethyl 2-[3-(2-cyano-4-trifluoromethylphenylthio)phenoxy]valeramide 2-[4-(3-Trifluoromethylphenylsulfinyl)phenoxy]propionic acid Triethanolammonium 2-[4-(2-trifluoromethylphenylsulfonyl)phenoxy]propionate Ethyl 3-[4-(2-methoxy-4-trifluoromethylphenylthio)-phenoxy]propionate 2-[4-(2-Nitro-4-trifluoromethylphenylsulfinyl)phenoxy]propionitrile Isobutyl 2-[4-(2-methyl-4-trifluoromethylphenylsulfonyl)phenoxy]butyrate 2-[4-(2-chloro-4-trifluoromethylthio)phenoxy]butyronitrile Ethyl 2-[4-(2-chloro-4-acetylphenylthio)phenoxy]propionate Ethyl 2-[4-(2-chloro-4-methanesulfonylphenylthio)-phenoxy]propionate Ethyl 2-[4-(2-acetyl-4-trifluoromethylphenylthio)-phenoxy]propionate Ethyl 2-[4-(2-amino-4-trifluoromethylphenylthio)phenoxy]propionate
Ethyl 2-[4-(2-fluoro-4-trifluoromethylphenylthiosulfinyl)phenoxy]propionate
n-Hexyl 2-[4-(2-methoxycarbonyl-4-trifluoromethylphenylsulfonyl)phenoxy]propionate
2-[4-(2-ethoxycarbonyl-4-trifluoromethylphenylthio)phenoxy]propionic acid and the like.

The compounds of the invention are useful for regulating plant growth. Typical plant responses include inhibition of vegetative growth in woody and herbaceous plants, control of flowering, control of fruiting, inhibition of seed formation, delay in maturation, and related growth regulatory responses. The growth regulatory action of the compounds of the present invention may be advantageously employed in various ways. The production of shorter and thicker stems in cereal grains may reduce the tendency toward lodging. Turf grasses may be maintained at a low height and the necessity for frequent mowing alleviated. The plant growth on embankments, such as roadsides, may be controlled to prevent erosion and at the same time maintain its aesthetic value. A dormant period may be produced in certain plants to minimize injury due to cold or freezing. The control of flowering and fruiting may be advantageous in the production of seedless fruit and for hybridization. Modifying the vegetative process or altering the time of flowering and fruiting may result in more advantageous harvest dates or increased or modified flower, fruit, or seed production. Useful chemical pruning of trees, shrubs, ornamentals and nursery stock may be obtained. Retardation of senescence of perishable fruits and vegetables can be effected to prolong storage life. Other applications of the compounds of the present invention will suggest themselves to those skilled in the art of agriculture.

When used as plant growth regulators, the compounds of the invention are applied to the plant, plant seeds, or plant habitat in an amount which will be sufficient to effect the desired plant response without causing a significant undesirable plant growth regulatory or phytotoxic response. Generally, the compounds of the invention will be applied to the plant or the plant habitat at a rate of about 0.01 to about 25 pounds per acre, and preferably about 0.1 to about 5 pounds per acre. When used as seed treatment agents, the compounds will usually be applied at a rate of about 0.25 to about 16 ounces per 100 pounds of seed, and preferably about 1 to about 4 ounces per 100 pounds of seed.

The compounds of the invention can be used as plant growth regulators either individually or in mixtures. For example, they can be used in combination with other plant growth regulators, such as auxins, gibberellins, ethylene-releasing agents such as ethephon, pyridones, cytokinins, maleic hydrazide, succinic acid 2,2-dimethylhydrazide, choline and its salts, (2-chloroethyl)trimethylammonium chloride, triiodobenzoic acid, tributyl-2,4-dichlorobenzylphosphonium chloride, polymeric N-vinyl-2-oxazolidinones, tri(dimethylaminoethyl)phosphate and its salts, and N-dimethylamino-1,2,3,6-tetrahydrophthalamic acid and its salts, and the like, and under some conditions may be used advantageously with other agricultural chemicals such as herbicides, fungicides, insecticides, and plant bactericides.

A compound of the invention can be applied to the growth medium or to plants to be treated either by itself or, as is generally done, as a component in a growth regulant composition or formulation which also comprises an agronomically-acceptable carrier. By "agronomically-acceptable carrier" is meant any substance which can be used to dissolve, disperse, or diffuse a compound in the composition without impairing the effectiveness of the compound and which by itself has no detrimental effect on the soil, equipment, crops, or agronomic environment. Mixtures of the compounds of the invention may also be used in any of these formulations. The compositions of the invention can be either solid or liquid formulations or solutions. For example, the compounds can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in foliar applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annula."

The compounds of the invention can be dissolved in any appropriate solvent. Examples of solvents which are useful in the practice of this invention include water, alcohols, ketones, aromatic hydrocarbons, halogenated hydrocarbons, dimethylformamide, dioxane, dimethyl sulfoxide, and the like. Mixtures of these solvents can also be used. The concentration of the solution can vary from about 2% to about 98% with a preferred range being about 20% to about 75%.

For the preparation of emulsifiable concentrates, the compound can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or water-soluble salt of a polyacrylic acid. The concentration of the active ingredient in emulsifiable concentrates of usually about 10% to 60% and in flowable emulsion concentrates, this can be as high as about 75%.

Wettable powders suitable for spraying, can be prepared by admixing the compound with finely divided solids, such as clays, inorganic silicates and carbonates, and silicas and incorporating wetting agents, sticking agents, and/or dispersing agents in such mixtures. The concentration of active ingredients in such formulations is usually in the range of about 20% to 98%, preferably about 40% to 75%. A dispersing agent may generally constitute about 0.5% to about 3% of the composition, and a wetting agent may generally constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. Once convenient method of preparing a dust is to dilute a wettable powder with a finely divided carrier. Dust concentrates containing about 20% to 80% of the active ingredient are commonly made and are subsequently diluted to about 1% to 10% use concentration.

Granular formulations can be prepared by impregnating a solid such as granular fuller's earth, vermiculite, ground corn cobs, seed hulls, including bran or other grain hulls, or similar material. A solution of one or more of the compounds in a volatile organic solvent can be sprayed or mixed with the granular solid and the solvent then removed by evaporation. The granular material can have any suitable size, with a preferable size range of 16 to 60 mesh. The active compound will usually comprise about 2 to 15% of the granular formulation.

The compounds of the invention can be applied as sprays by methods commonly employed, such as conventional hydraulic sprays, aerial sprays, and dusts. For low-volume applications a solution of the compound is usually used. The dilution and volume of application will usually depend upon such factors as the type of equipment employed, the method of application, and the area to be treated.

The compounds of Formula I used in the invention or their precursors are prepared by several different reaction routes. In one typical synthetic method a halobenzene of the formula

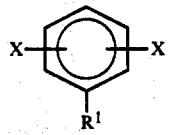

(II)

wherein X and $X^1$ are as defined above and $R^1$ is a halogen atom, preferably a fluorine, chlorine, or bromine atom, is reacted with a phenol of the formula

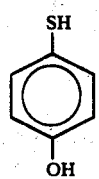

(III)

to form a compound of the formula

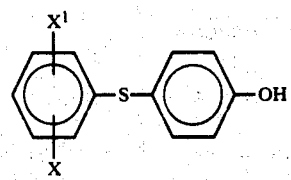

(IV)

wherein X and $X^1$ are a defined above. This reaction is generally carried out at a temperature of about 25° to about 150° C., in the presence of a base such as potassium hydroxide, sodium hydroxide, potassium carbonate, sodium carbonate, sodium hydride or the like, with an aprotic polar solvent, such as dimethylsulfoxide, dimethylformamide, sulfolane, hexamethylphosphoric triamide, 1-methyl-2-pyrrolidinone, and the like. The phenol of Formula IV is then reacted with a compound of the formula

(V)

wherein $R^2$ is a chlorine or a bromine atom, and Z and $Z^1$ are as defined above. This reaction is generally carried out at a temperature of about 25° to about 150° C., in the presence of a base, such as potassium hydroxide, sodium hydroxide, potassium carbonate, sodium carbonate, or the like with an aprotic polar solvent, such as dimethylsulfoxide, dioxane, a ketone, such as acetone, methyl ethyl ketone, or the like, acetonitrile ethylene glycol dimethyl ether, tetrahydrofuran, and the like.

The phenol of Formula IV can also be prepared by reacting a compound of Formula II with a compound of the formula

(VI)

wherein $R^3$ is an allyl group or a benzyl group. This reaction is carried out under the same conditions as the reaction of compounds II and III. The resultant diphenyl sulfide is then hydrogenated using palladium on charcoal, platinum oxide, or the like as a catalyst, in an alcohol, such as methanol or ethanol, ethyl acetate, acetic acid, or the like as a solvent, at ambient temperatures, or at a temperature of about 0° to about 120° C., to yield the phenol. When $R^3$ is a methyl group, the compound of Formula VI can be reacted with a compound of Formula II under the same conditions as the reaction of compounds II and III, or a cuprous salt of this compound can be reacted with a compound of Formula II in which $R^1$ is a bromine atom. The resultant anisole can then be dealkylated by conventional techniques such as reaction into hydrogen bromide in refluxing acetic acid to yield the phenol.

The compounds of Formula I in which $Z^1$ is a carboxy group can be prepared by hydrolyzing a compound of the invention in which $Z^1$ is a cyano group, a carbamoyl group, or a carbalkoxy group. The hydrolysis can be either acid-catalyzed, using sulfuric acid, anhydrous hydrochloric acid in methanol, acetic acid/boron trifluoride, or similar acid catalyst, or base-catalyzed using potassium hydroxide in methanol, barium hydroxide in methanol, or similar base catalyst, optionally with an appropriate inert solvent, at a temperature of about 20° to about 130° C. Suitable reaction conditions for carrying out the desired hydrolysis can be varied, depending on the group to be hydrolyzed and the various substituents on the diphenyl sulfide nucleus, and such modifications will be apparent to those skilled in the art.

The diphenyl sulfides of Formula I can also be prepared by reacting a phenol of Formula III with cuprous oxide to produce the cuprous salt of the thiophenol. This reaction can be carried out, for example, in refluxing ethanol. The cuprous salt is generally not isolated, but reacted directly with a halobenzene of Formula II in which $R^1$ is a bromine atom, in a solvent such as quinoline, dimethylformamide or the like, in the presence of a nitrogen base such as pyridine, quinoline or the like, at a temperature of about 50° to about 200° C. The resulting phenol is then further reacted as noted above to produce the desired diphenyl sulfide. Other suitable methods for preparing the diphenyl sulfides of the invention include displacement of aromatic diazonium salts with a salt, such as a sodium salt, of a thiophenol of Formula III. Diphenyl sulfides, sulfoxides, and sulfones of the invention can also be prepared by the reaction of an appropriate aromatic sulfenyl, sulfinyl, or sulfonyl halide with a substituted phenol or anisole.

The compounds of Formula I in which Y is a sulfinyl group can be prepared by oxidizing the corresponding diphenyl sulfide of Formula I or IV using an oxidizing agent such as an excess or equimolar amount of sodium periodate in methanol/water, at about 0° to about 60° C., or one equivalent of hydrogen peroxide in acetic acid, at about 0° to about 50° C., optionally using an acidic catalyst, such as sulfuric acid. Compounds of the invention in which Y is a sulfonyl group can be prepared by oxidizing the corresponding diphenyl sulfide, for example, with at least two equivalents of hydrogen peroxide in acetic acid, at about 0° to about 120° C., optionally using an acidic catalyst such as sulfuric acid. The compounds of Formula I and their preparation are disclosed and claimed in pending application U.S. Ser. No. 710,074, of Johnson et al., filed on July 30, 1976, which is incorporated herein by reference. Other methods which are apparent to those skilled in the art for preparing the compounds of the invention or their precursors can also be used.

The following examples will further illustrate this invention, but are not intended to limit it in any way. Examples 1, 2, and 12 show illustrative procedures for the preparation of typical compounds used in the methods of the invention. All temperatures are in degrees Celsius and all parts and percentages are by weight unless otherwise indicated.

EXAMPLE 1

Preparation of Ethyl 2-[4-(2-Chloro-4-trifluoromethylphenylthio)-phenoxy]-propionate To a stirred slution containing 12.6 g. (0.1 mole) of 4-mercaptophenol in 75 ml. of dimethylformamide is added 6.6 g. (0.1 mole) of 85% potassium hydroxide pellets in one portion at 25°. The resultant mixture is heated until all of the potassium hydroxide has dissolved, whereupon it is cooled to about 80° and 21.6 g. (0.1 mole) of 3,4-dichlorobenzotrifluoride is added over a period of 15 minutes. The addition is accompanied by an immediate precipitation of potassium chloride. the resultant slurry is heated at 100° to effect complete reaction, at which time it is cooled to 25°, diluted to a volume of 300 ml. with a dilute hydrochloric acid solution, and extracted three times with ether. The combined organic extracts are washed with a dilute hydrochloric acid solution, water, a saturated sodium chloride solution, dried with anhydrous magnesium sulfate, and concentrated in vacuo. Purification of the crude white solid is effected by recrystallization from hexane-ether to afford 17.1 g. of 4-(2-chloro-4-trifluoromethylphenylthio)phenol, mp 118°–120°.

A mixture containing 6.09 g. (0.02 mole) of 4-(2-chloro-4-trifluoromethylphenylthio)phenol, 3.04 g. (0.22 mole) of potassium carbonate, 3.62 g. (0.02 mole) of ethyl 2-bromopropionate, and 100 ml. of dimethyl sulfoxide is stirred at 25° for sufficient time to affect complete reaction, as indicated by vapor-phase chromatographic techniques. Upon dilution with 500 ml. of water and 100 ml. of a 3.0 molar hydrochloric acid solution the product is extracted with ether. The combined organic extracts are washed with a 5% potassium carbonate solution, water, a saturated sodium chloride solution, dried with anhydrous magnesium sulfate, and concentrated in vacuo. Removal of the last traces of solvent is accomplished by subjecting the yellow liquid to high vacuum (0.05 mm) at 70° to afford 7.95 g. of ethyl 2-[4-(2-chloro-4-trifluoromethylphenylthio)-phenoxy]propionate. Recrystallization from methanol affords white crystals, mp 64.5°–66.5°.

EXAMPLE 2

Preparation of Ethyl 2-[4-(2-nitro-4-trifluoromethylphenylthio)phenoxy]propionate A mixture containing 12.6 g. (0.10 mole) of 4-mercaptophenol, 7.15 g. (0.05 mole) of copper (I) oxide, and 100 ml. of absolute ethanol is heated at reflux under an atmosphere of dry nitrogen until conversion to the copper thiphenate is complete, as indicated by discharge of the reddish color of the copper (I) oxide. The resultant yellow mixture is cooled to 25°, 27.0 g. (0.10 mole) of 4-bromo-3-nitrobenzotrifluoride, 100 ml. of quinoline, and 10 ml. of pyridine are added, and the reaction vessel is equipped with a Newman still head. The reaction is now slowly heated with concomitant removal of the ethanol to 90° and maintained at this temperature until the conversion is complete, as indicated by vpc techniques. The dark liquid is cooled to 70° C., cautiously poured into 500 ml. of an ice cold 3.0 molar hydrochloric acid solution, and filtered, whereupon the residue is extracted with several portions of ether. the combined ether extracts are washed with a 3.0 molar hydrochloric acid solution, water until neutral, a saturated sodium chloride solution, dried (magnesium sulfate), and concentrated in vacuo to afford a quantitative yield of crude product as a dark solid. Recrystallization foam ether-hexane provides yellow crystals, mp 131°–134° of 4-(2-nitro-4-trifluoromethylphenylthio)-phenol. This phenol is then reacted with 2-bromopropionate by the procedure of Example 3 above to provide the desired ethyl 2-[4-(2-nitro-4-trifluoromethylphenylthio)phenoxy]propionate, mp 63°–64° C.

EXAMPLE 12

Preparation of Ethyl 2-[4-(2-trifluoromethylphenylsulfinyl)phenoxy]propionate

To a stirred solution containing 7.4 g. (0.020 mole) of ethyl 2-[4-(2-trifluoromethylphenylthio)phenoxy]propionate and a catalytic amount of sulfuric acid (3 drops) in 50 ml of glacial acetic acid is added a solution containing 2.23 g. (0.021 mole) of 32% hydrogen peroxide in 10 ml. of glacial acetic acid over a period of several minutes at 25°. The resultant solution is stirred for 24 hours under ambient conditions, at which time the reaction is essentially complete. After the reaction mixture is treated with sodium bisulfite to destroy any excess peroxide the solvent is removed in vacuo at 40° and the residue taken-up in ether. The ethereal solution is washed with a 5% potassium carbonate solution until basic, water until neutral, a saturated sodium chloride solution, dried with magnesium sulfate, and concentrated in vacuo to give 6.85 g. of material. The last traces of solvent are removed by exposure to high vacuum (0.1 mm) at 70° to afford ethyl 2-[4-(2-trifluoromethylphenylsulfinyl)phenoxy]propionate.

Following procedures similar to those set forth in Examples 1 to 3 or otherwise described above, the following compounds are prepared (4) Ethyl 2-[4-(2-chloro-4-trifluoromethylphenylsulfinyl)phenoxy]propionate
(5) Ethyl 2-[4-(2-chloro-4-trifluoromethylphenylsulfonyl)phenoxy]propionate
(6) Ethyl 2-[4-(2-trifluoromethylphenylthio)phenoxy]propionate
(7) Ethyl 2-[4-(3-trifluoromethylphenylthio)phenoxy]propionate
(8) Ethyl 2-[4-(4-trifluoromethylphenylthio)phenoxy]propionate
(9) Ethyl 2-[4-(2-cyano-4-trifluoromethylphenylthio)phenoxy]propionate
(10) Ethyl 2-[4-(4-nitrophenylthio)phenoxy]propionate
(11) Ethyl 2-[4-(4-chlorophenylthio)phenoxy]propionate
(13) Ethyl 2-[4-(3-trifluoromethylphenylsulfinyl)phenoxy]propionate
(14) Ethyl 2-[4-(2-carbamoyl-4-trifluoromethylphenylsulfinyl)phenoxy]propionate
(15) Ethyl 2-[4-(4-nitrophenylsulfinyl)phenoxy]propionate
(16) Ethyl 2-[4-(4-trifluoromethylphenylsulfinyl)phenoxy]propionate
(17) Ethyl 2-[4-(4-chlorophenylsulfinyl)phenoxy]propionate
(18) Ethyl 2-[4-(2-chloro-5-trifluoromethylphenylthio)phenoxy]propionate, oil
(19) 2-[4-(2-Cyano-4-trifluoromethylphenylthio)phenoxy]propionic acid, mp 113°–115°
(20) methyl amide of (19), mp 170°–172°
(21) iso-propyl amide of (19), mp 159°–160°
(22) tert-butyl amide of (19), mp 124°–129°
(23) allyl amide of (19), mp 115°–117°
(24) benzyl amide of (19), oil
(25) morpholinoamide of (19), mp 62°–66°
(26) phenyl amide of (19), mp 152°–154°
(27) dimethyl amide of (19), mp 106°–108.5°
(28) diallyl amide of (19), oil
(29) methyl (2-hydroxyethyl)amide of (19), oil
(30) Ethyl 2-[3-(2-cyano-4-trifluoromethylphenylthio)phenoxy]propionate, oil
(31) 2-[4-(2-Cyano-4-trifluoromethylphenylthio)phenoxy]propionyl chloride, oil
(32) Ethyl 2-[4-(2-fluoro-4-trifluoromethylphenylthio)phenoxy]propionate, oil
(33) 2-[4-(2-Chloro-4-trifluoromethylphenylthio)phenoxy]propioamide, mp 155°–157°
(34) Ethyl 2-[4-(2-chloro-4-trifluoromethylphenylthio)phenoxy]isobutyrate, oil
(35) N-methyl 2-[4-(2-chloro-4-trifluoromethylphenylthio)phenoxy]propanamide, mp 111°–112°
(36) Ethyl 2-[4-(2-nitro-4-trifluoromethylphenylthio)phenoxy]propionate, mp 63°–64°
(37) Ethyl 2-[4-(2-nitro-4-trifloromethylphenylsulfinyl)phenoxy]propionate, oil
(38) Ethyl 2-[4-(2-cyano-4-trifluoromethylphenylthio)phenoxy]acetate, mp 58°–59°
(39) 2-[4-(2-cyano-4-trifluoromethylphenylthio)phenoxy]propanamide, mp 139°–146.5°
(40) 2-[4-(2-cyano-4-trifluoromethylphenylthio)phenoxy]propionitrile, oil
(41) Ethyl 2-[4-(2-bromo-4-trifluoromethylphenylthio)phenoxy]propionate, mp 58.5°–60°
(42) Ethyl 2-[4-(3-trifluoromethyl-4-chlorophenylthio)phenoxy]propionate, oil
(43) Ethyl 2-[4-(3,5-bis(trifluoromethyl)phenylthio)phenoxy]propionate, mp 43°–40°

The following examples show typical applicatins of the compounds of the invention as plant growth regulating agents.

EXAMPLE 44

Inhibition of Vegetative Growth of Polebean Plants

This example shows the application of compounds of the invention to inhibit new vegetative growth and provide height reduction in crops such as cotton and soybeans. Such growth inhibition may produce more compact plants, shorten their maturity or, in soybeans, reduce lodging or induce more pod set.

Four or five polebean seeds (var. Kentucky Wonder) are planted in six-inch pots. Shortly after the plants have emerged from the soil, the stems of all but the two most desirable plants in each pot are severed. When the growing plants have fully expanded primary leaves, they are treated with a solution of the indicated compound in acetone by foliar application at a rate of 0.25 pounds (50 gallons) per acre. Seven days after the chemical treatment, the plant height is measured and compared to that of an untreated control to determine the percent inhibition which has resulted from the treatment. Table I lists typical compounds of the invention, their melting points (if applicable), and the percent inhibition compared to an untreated control. These results are calculated from the average plant height of four treated plants compared to the average plant height of eight untreated control plants.

TABLE I

INHIBITION OF POLEBEAN GROWTH

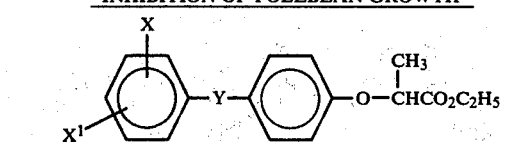

| Compound No. | X | $X^1$ | Y | m.p.° | % Inhibition |
|---|---|---|---|---|---|
| 1 | 2-Cl | 4-$CF_3$ | S | 64.5–65.5 | 60 |
| 4 | 2-Cl | 4-$CF_3$ | SO | oil | 34 |
| 5 | 2-Cl | 4-$CF_3$ | $SO_2$ | oil | 7 |
| 6 | 2-$CF_3$ | H | S | oil | 24 |
| 7 | 3-$CF_3$ | H | S | oil | 53 |
| 8 | 4-$CF_3$ | H | S | oil | 36 |
| 9 | 2-CN | 4-$CF_3$ | S | 58–61 | 18 |
| 10 | 4-$NO_2$ | H | S | oil | * |
| 11 | 4-Cl | H | S | oil | 19 |
| 12 | 2-$CF_3$ | H | SO | oil | 14 |
| 13 | 3-$CF_3$ | H | SO | oil | 5 |
| 14 | 2-$CONH_2$ | 4-$CF_3$ | SO | 171–181 | 22 |
| 15 | 4-$NO_2$ | H | SO | 123–126.5 | 12 |
| 16 | 4-$CF_3$ | H | SO | oil | 31 |
| 17 | 4-Cl | H | SO | oil | 26 |

*treated plants were 2% taller than control

EXAMPLE 45

Inhibition of Vegetative Control of Corn Plants

Following the procedure of Example 4, corn plants (var. XL-45A) are treated with compounds of the invention at the 2 to 5 true leaf stage, and evaluated for growth inhibition one month after treatment. Table II summarizes results from these tests. All data is based on an average of six plants at each rate for each compound.

TABLE II

INHIBITION OF CORN GROWTH

| Compound No.* | Rate (lb/A) | % Inhibition | Phytotoxicity** |
|---|---|---|---|
| 1 | 0.25 | 21 | 2.5 |
|  | 1 | — | 8 |
| 4 | 0.25 | 19 | 0 |
|  | 1 | 20 | 0 |
|  | 2 | 21 | 0.5 |
|  | 4 | 24 | 0.5 |

*as in Table I
**0 = no injury; 10 = complete kill

EXAMPLE 46

Snapbean Yield Promotion

Four to five snapbean seeds (Dwarf Horticultural) are plants in six inch pots. After the plants have reached desirable size (about 9 days after planting), the stems of all but the two most desirable plants in each pot are severed. When flower buds have formed (about 7 days before flowering), the plants are treated with ethyl 2-[4-(2-chloro-4-trifluoromethylphenylsulfinyl)phenoxy]propionate at rates of 0.125 and 0.25 pounds per acre. The mature beans are harvested, counted, and weighed. At a treatment rate of 0.125 pounds per acre, an average of eight plants gave a 29% increase in number of bean pods and a 20% increase in pod weight compared to an average of eight untreated plants. At an application rate of 0.25 pounds per acre, the average increases in the eight treated plants were 13% and 8% respectively.

EXAMPLE 47

Inhibition of Vegetative Growth of Soybeans

Four to five soybean seeds (var. William) are planted in six-inch pots. Shortly after the plants have emerged from the soil, the stems of all but the most desirable plant in each pot are severed. When the growing plants are in the 2 to 3 trifoliate stage, they are treated with ethyl 2-[4-(2-chloro-4-trifluoromethylphenyl sulfinyl)phenoxy]propionate at application rates of 0.125 and 0.25 pounds per acre. Sixty days after treatment, the growth of the treated plants (three plants at each rate of application) during this period is compared to the growth of three untreated control plants during the same period. At an application rate of 0.125 pounds per acre, 31% inhibition was noted and at an application rate of 0.25 pounds per acre, 38% inhibition was noted compared to the untreated control, and the treated plants showed slight phytotoxicity.

EXAMPLE 48

Inhibition of Growth in Woody Species

Grape, apple, and silver maple seedlings are individually planted in three-inch pots. After the heights of all untreated seedlings have been measured, half of the plants are treated by foliar application with ethyl 2-[4-(2-trifluoromethylphenylsulfinyl)phenoxy]propionate, dissolved in acetone at an application rate of 1 and 4 pounds (50 gallons) per acre. Approximately three weeks after treatment, the height of the seedlings are again measured, and the growth of the treated seedlings during the three-week period is compared to the growth of a like number of untreated seedlings during the same period.

Table III summarizes results from these tests.

TABLE III

| Plants | Inhibition of Woody Species | | |
|---|---|---|---|
|  | Rate (il/A) | % Inhibition | Phytotoxicity** |
| Grape | 1 | 14 | 2 |
|  | 4 | 90 | 6 |
| Apple | 1 | 26 | 0 |
|  | 4 | 43 | 0 |
| Maple | 1 | 71 | 2 |
|  | 4 | 40 | 5 |

*Grape — average of 5 plants; Apple — average of 2 plants; Maple — average of 3 plants
**as in Table II It should be understood that changes and variations can be made without departing from the spirit and scope of the invention as defined by the appended claims.

We claim:

1. A method for regulating plant growth which comprises applying to a plant, to plant seeds, or to the locus of a plant an effective amount of a compound of the formula

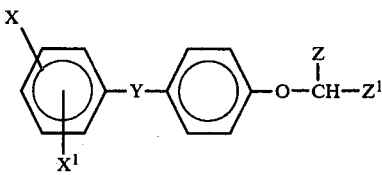

wherein

X is a hydrogen atom, a halogen atom, a trifluoromethyl group, or a nitro group, $X^1$ is a hydrogen atom, a halogen atom, a trifluoromethyl group, a cyano group, a carbamoyl group, a methyl group, a methoxy group, a ($C_1$–$C_4$ alkoxy carbonyl group, a methylcarbonyl group, a methanesulfonyl group, or an amino group, Y is a group of the formula —S—, —SO—, or —$SO_2$, Z is a hydrogen atom or a ($C_1$–$C_4$)alkyl group, and $Z^1$ is a carboxy group, or an agronomically acceptable salt thereof, a cyano group, or a group of the formula —COR, wherein R is a ($C_1$–$C_{12}$)alkoxy group, a ($C_7$–$C_{12}$)aralkoxy group, a ($C_1$–$C_6$)alkoxy ($C_1$–$C_6$)alkoxy group, a ($C_3$–$C_5$)alkenoxy group, an amino group, a ($C_1$–$C_4$)alkylamino group, or a di($C_1$–$C_4$)alkylamino group.

2. The method of claim 1 wherein X is a halogen atom or a trifluoromethyl group and $X^1$ is a hydrogen atom, a halogen atom, or a cyano group.

3. The method of claim 2 wherein Y is a group of the formula —S—.

4. The method of claim 3 wherein Z is a methyl group and $Z^1$ is a group of the formula —COR, wherein R is a ($C_1$–$C_{12}$)alkoxy group.

5. The method of claim 4 wherein X is a trifluoromethyl group and $X^1$ is a hydrogen atom or a halogen atom.

6. The method of claim 2 wherein Y is a group of the formula —SO—.

7. The method of claim 6 wherein Z is a methyl group and $Z^1$ is a group of the formula —COR, wherein R is a $(C_1-C_{12})$alkoxy group.

8. The method of claim 7 wherein X is a trifluoromethyl group.

9. The method of claim 8 wherein $X^1$ is a hydrogen atom.

10. The method of claim 9 wherein X is a 2-trifluoromethyl group.

11. The method of claim 9 wherein the plant is a woody species.

12. The method of claim 8 wherein $X^1$ is a halogen atom.

13. The method of claim 12, wherein X is a trifluoromethyl group and $X^1$ is a halogen atom.

14. The method of claim 13 wherein X is a 4-trifluoromethyl group and $X^1$ is a 2-chlorine atom.

15. The method of claim 12 wherein the plant is soybeans.

* * * * *